(12) United States Patent
Jansen (10) Patent No.: US 9,968,064 B2
(45) Date of Patent: May 15, 2018

(54) SPINACH HYBRID 51-521 RZ

(71) Applicant: RIJK ZWAAN ZAADTEELT EN ZAADHANDEL B.V., De Lier (NL)

(72) Inventor: Johannes Petrus Antonius Jansen, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 41 days.

(21) Appl. No.: 14/951,583

(22) Filed: Nov. 25, 2015

(65) Prior Publication Data

US 2016/0150753 A1 Jun. 2, 2016

Related U.S. Application Data

(60) Provisional application No. 62/085,507, filed on Nov. 29, 2014.

(51) Int. Cl.
*A01H 5/12* (2018.01)
*C12Q 1/68* (2018.01)
*A23L 19/00* (2016.01)

(52) U.S. Cl.
CPC .............. *A01H 5/12* (2013.01); *A23L 19/03* (2016.08); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2014/0090096 A1* 3/2014 Baerends ................. A01H 5/12
800/260

* cited by examiner

*Primary Examiner* — Cathy Kingdon Worley
*Assistant Examiner* — Russell T Boggs
(74) *Attorney, Agent, or Firm* — Vedder Price P.C.; Thomas J. Kowalski; Deborah L. Lu (57) ABSTRACT

The present invention relates to a *Spinacia oleracea* seed designated 51-521 RZ, which exhibits a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15. The present invention also relates to a *Spinacia oleracea* plant produced by growing the 51-521 RZ seed. The invention further relates to methods for producing the spinach cultivar, represented by spinach variety 51-521 RZ.

21 Claims, 1 Drawing Sheet

Fig. 1

Erect  Semi-Erect  Flat

Fig. 2

1 = Elliptic  2 = Circular  3 = Ovate  4 = Three-sided

5 = Five-sided  6 = Arrow-shaped  7 = Asymmetrical

Fig. 3

1 = Round  2 = Round-pointed  3 = Pointed

SPINACH HYBRID 51-521 RZ

RELATED APPLICATIONS AND INCORPORATION BY REFERENCE

This application claims priority to U.S. provisional patent application Ser. No. 62/085,507, filed Nov. 29, 2014.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated herein by reference, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new hybrid spinach (*Spinacia oleracea*) variety which exhibits a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

BACKGROUND OF THE INVENTION

Spinach (*Spinacia oleracea*) is a flowering vegetable plant belonging to the family Amaranthaceae. It is native to Southwestern and Central Asia, but today spinach is cultivated worldwide, mainly in temperate regions. Spinach plants are cultivated for their highly nutritious leaves. The leaves are extremely rich in antioxidants, a good source of vitamins such as A, B6, C, E, K and folate, and minerals such as calcium, iron, magnesium and potassium.

The edible part of the spinach plant is a compact rosette shape of leaves attached to a short stem. The leaves are produced during the first stage of the plant's life cycle, the vegetative rosette stage. The second stage is the flowering stage, or the bolting stage. When bolting occurs, there is growth of an elongated stalk with flowers growing from within the main stem of the plant. Once the plant has reached the bolting stage, it is no longer possible to harvest marketable leaves. The plant will allocate its resources to flowering instead of leaf production, which will ultimately cause the leaves to wither. Fast bolting is thus an undesired trait in the production of leafy vegetables such as spinach. Therefore, slower bolting is preferred by growers in order to optimize yield.

There are three basic types of spinach, namely savoy, semi-savoy, and smooth. The savoy type spinach has dark green, crinkly and curly leaves. The semi-savoy type spinach is a hybrid variety with slightly crinkled leaves. Smooth type spinach has broad, smooth leaves.

The leaves of a spinach plant are usually sold loose, bunched, in pre-packaged bags, canned or frozen. Each of these products requires its own type of leaves. The smooth and some of the semi-savoy varieties are predominantly used in processed products such as canned or frozen spinach, while the semi-savoy and savoy types are especially used for the fresh market. Smooth leaf varieties are better suited for processing purposes than semi-savoy and savoy varieties, because they are easier to clean and prepare for canning and freezing. Savoy leaf varieties, on the other hand, are preferred in the fresh market because the leaves pack looser than the smooth leaf varieties and are less likely to wilt or turn yellow.

The growth habit of spinach varieties can be classified in three different categories, flat or prostate, semi-erect, and upright or erect. For mechanical harvest an upright or erect habit is preferred in order to reduce soil contamination. Especially for varieties with savoy type leaves this is an important character, because the soil is difficult to remove from curly leaves. Sometimes even plant growth regulators are applied before harvest to cause a more upright leaf growth and reduce the risk of soil contamination. More upright varieties are thus desired by growers to reduce contamination and costs for spraying plant regulators.

Downy mildew is probably the most widespread and potentially destructive global disease of spinach. The causal agent of downy mildew on various Amaranthaceae, including spinach, is regarded as a single species, *Peronospora farinosa*. In particular, *Peronospora farinosa* f. sp. *spinaciae* infects spinach. Initial symptoms of downy mildew consist of dull to bright yellow necrotic lesions that appear on the leaves of infected spinach plants. With time the lesions can enlarge and become tan and dry. The infection can spread very rapidly, and it can occur both in glasshouse cultivation and in soil cultivation, resulting in widespread crop damage. In addition to the loss of quality of the leaves due to the lesions, downy mildew can also cause breakdown and rot of the infected leaves if they packaged in bags and cartons.

The optimal temperature for formation and germination of *P. farinosa* f. sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of ≥80%, and within 6 and 13 days after infection mycelium growth can be observed. Oospores of *P. farinosa* can survive in the soil for up to 3 years, or as mycelium in seeds or living plants. Although some fungicide treatments may be effective, they are costly and cause ecological pollution.

In recent years various resistance genes have been identified that provide spinach plants with a resistance against downy mildew. However, it has been observed that previously resistant spinach cultivars can again become susceptible to the fungus. Investigations revealed that the cultivars themselves had not changed, and that the loss of downy mildew resistance must therefore be due to *P. farinosa* overcoming the resistance in these spinach cultivars. The downy mildew races (also called physios, isolates, or strains) that were able to infect resistant spinach cultivars were collected in a differential reference set, which can be used to test spinach cultivars for resistance. The differential set may comprise a series of spinach cultivars (hybrids) that have different resistance patterns to the currently identified pathogenic races.

Currently there are 15 officially recognised races of *Peronospora farinosa* f. sp. *spinaciae*, designated races Pfs 1 to Pfs15 (Irish et al. Phtypathol. Vol. 98 pg. 894-900, 2008; Plantum NL (Dutch association for breeding, tissue culture, production and trade of seed and young plants) press release, "Benoeming van Pfs: 14, een nieuwe fysio van valse meeldauw in spinazie", Sep. 19, 2012; Report Jim Correl (Univ. Arkansas) and Steven Koike (UC Cooperative Extension, Monterey County), "Race Pfs: 14—Another new race of the spinach downy mildew pathogen", Sep. 18, 2012; Plantum NL press release, "Denomination of Pfs: 15, a new race of downy mildew in spinach", Sep. 2, 2014). Races 4 to 14 were identified between 1990 and 2012, while only recently another new *Peronospora* isolate has been identified, termed UA4712, which subsequently has been officially named Pfs15 by the International Working Group on Peronospora (IWGP) (Plantum NL (Dutch association for breeding, tissue culture, production and trade of seed and young plants) press release, "Denomination of Pfs: 15, a new race of downy mildew in spinach", Sep. 2, 2014. All 15 officially recognized Pfs races are publicly available from the Department of Plant Pathology, University of Arkansas, Fayetteville, Ariz. 72701, USA, and also from NAK Tuinbouw, Sotaweg 22, 2371 GD Roelofarendsveen, the Netherlands.

Newly identified *Peronospora* races can break the resistance of many spinach varieties that are currently used commercially worldwide, and they thus pose a serious threat to the productivity of the spinach industry. For this reason new resistance genes are very valuable assets. In order to confer a resistance that is as broad as possible, i.e. that confers resistance to as many Pfs races as possible, preferable to all known Pfs races, it is very useful to be able to stack different resistance genes against *Peronospora* infection in spinach. This is achieved by stacking various resistance genes which have overlapping resistance patterns. In this way it becomes more difficult for the pathogen to overcome the resistance. Such a combination of different resistance genes on one gene segment is also highly desirable. It is much easier if the resistance genes can be inherited as a single dominant loci, because in that case the resistance pattern that is conferred by the dominant resistance gene cannot segregate in the progeny of the cross, and will always inherit as one single set of resistances to various pathogenic races. One such resistance gene, designated R6, is a single dominantly inherited resistance gene in spinach that confers resistance to at least *Peronospora farinosa* f. sp. *spinaciae* races Pfs1, Pfs2, Pfs3, Pfs4, Pfs5, Pfs6, Pfs9, Pfs11, Pfs12, Pfs13 and Pfs14 (See generally U.S. application Ser. No. 13/774,633 and U.S. application Ser. No. 13/872,011).

Another important destructive foliar disease in spinach is anthracnose. Spinach anthracnose is caused by the fungus *Colletotrichum dematium* f. sp. *spinaciae*. Early symptoms of anthranose are small lesions and necrotic areas on leaves. These lesions advance to form large necrotic areas in the leaves in which characteristic structures of the fungus may be observed using a 10-20× hand lens or a stereoscope. Spores are produced abundantly during wet conditions. They are spread by wind and splashing water. Anthracnose of spinach is difficult to control. The increased use of wide densely planted beds and overhead irrigation creates an ideal environment for disease development. Tolerant varieties are not available, and chemical treatments are not effective. This disease is responsible for significant economic losses in spinach production areas. Obtaining spinach varieties with a level of genetic resistance to anthracnose is thus highly desired.

Citation or identification of any document in this application is not an admission that such document is available as prior art to the present invention.

SUMMARY OF THE INVENTION

There exists a need, therefore, for a hybrid spinach variety which exhibits a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

The present invention addresses this need by providing a new type of spinach (*Spinacia oleracea*) variety, designated 51-521 RZ. Spinach cultivar 51-521 RZ exhibits a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

The present invention provides seeds of spinach cultivar 51-521 RZ, which have been deposited with the National Collections of Industrial, Marine and Food Bacteria (NCIMB) in Bucksburn, Aberdeen AB21 9YA, Scotland, UK and have been assigned NCIMB Accession No. 42335.

In one embodiment, the invention provides a spinach plant designated 51-521 RZ, representative seed of which have been deposited under NCIMB Accession No. 42335, wherein said spinach plant may comprise a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

In one embodiment, the invention provides a spinach plant designated 51-521 RZ wherein said spinach plant may comprise a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15 and round pointed mature leaves, representative seed of which have been deposited under NCIMB Accession No. 42335.

In one embodiment, the invention provides a spinach plant designated 51-521 RZ, representative seed of which have been deposited under NCIMB Accession No. 42335.

In one embodiment, the invention provides a seed of a spinach plant designated 51-521 RZ, representative seed of which having been deposited under NCIMB Accession No. 42335, wherein said plant may comprise at least the following combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

In an embodiment of the present invention, there also is provided parts of a spinach plant of the invention, which may include parts of a spinach plant exhibiting a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15, or parts of a spinach plant having any of the aforementioned resistance(s) and a combination of traits including one or more morphological or physiological characteristics tabulated herein, including parts of hybrid spinach variety 51-521 RZ, wherein the plant parts are involved in sexual reproduction, which include without limitation, a microspore, pollen, an ovary, an ovule, an embryo sac or egg cell and/or wherein the plant parts are suitable for vegetative reproduction, which include, without limitation, a cutting, a root, a stem, a cell or a protoplast and/or wherein the plant parts are tissue culture of regenerable cells in which the cells or protoplasts of the tissue culture are derived from a tissue such as, for example and without limitation, a leaf, pollen, an embryo, a cotyledon, a hypocotyl, a meristematic cell, a root, a root tip, an anther, a flower, a seed or a stem. The plants of the invention from which such parts can come from include those wherein representative seed of which has been deposited under NCIMB Accession No. 42335 or hybrid spinach variety or cultivar designated 51-521 RZ, as well as seed from such a plant, plant parts of such a plant (such as those mentioned herein) and plants from such seed and/or progeny of such a plant, advantageously progeny exhibiting such combination of such traits, each of which, is within the scope of the invention; and such combination of traits.

In another embodiment there is a plant grown from seeds, representative seed of which having been deposited under NCIMB Accession No. 42335.

In a further embodiment there is a plant regenerated from the above-described plant parts or regenerated from the above-described tissue culture. Advantageously such a plant may have morphological and/or physiological characteristics of hybrid spinach variety 51-521 RZ and/or of a plant grown from seed, representative seed of which having been deposited under NCIMB Accession No. 42335—including without limitation such plants having all of the morphological and physiological characteristics of hybrid spinach variety 51-521 RZ and/or of plant grown from seed, representative seed of which having been deposited under NCIMB Accession No. 42335. Advantageously, such a plant demonstrates the traits of fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

Accordingly, in still a further embodiment, there is provided a spinach plant having all of the morphological and physiological characteristics of hybrid spinach variety 51-521 RZ, representative seed of which having been deposited under NCIMB Accession No. 42335. Such a plant can be grown from the seeds, regenerated from the above-described plant parts, or regenerated from the above-described tissue culture. A spinach plant having any of the aforementioned resistance(s), and one or more morphological or physiological characteristics recited or tabulated herein, and a spinach plant advantageously having all of the aforementioned resistances and the characteristics recited and tabulated herein, are preferred. Parts of such plants— such as those plant parts above-mentioned—are encompassed by the invention.

In an embodiment of the present invention, there is provided a spinach plant exhibiting a combination of traits which may comprise fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15, and having genetic material for so exhibiting the combination of traits; wherein the genetic information is as contained in a plant, representative seed of which having been deposited under NCIMB Accession No. 42335.

In one embodiment, there is provided a method for producing a progeny of hybrid spinach variety 51-521 RZ which may comprise crossing the plant designated 51-521 RZ with itself or with another spinach plant, harvesting the resultant seed, and growing said seed.

In a further embodiment, there is provided progeny of spinach cultivar 51-521 RZ produced by sexual or vegetative reproduction, grown from seeds, regenerated from the above-described plant parts, or regenerated from the above-described tissue culture of the spinach cultivar or a progeny plant thereof, representative seed of which having been deposited under NCIMB Accession No. 42335. The progeny may have any of the aforementioned resistance(s), and one or more morphological or physiological characteristics recited or tabulated herein, and a progeny plant advantageously having all of the aforementioned resistances and the characteristics recited and tabulated herein, is preferred. Advantageously, the progeny demonstrate the traits of fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15 and has genetic material for so exhibiting the combination of traits; wherein the genetic information is as contained in a plant, representative seed of which having been deposited under NCIMB Accession No. 42335.

Progeny of the hybrid spinach variety 51-521 RZ may be modified in one or more other characteristics, in which the modification is a result of, for example and without limitation, mutagenesis or transformation with a transgene.

In another embodiment the invention relates to a method of producing an inbred spinach plant derived from a plant of the invention of which representative seed has been deposited under NCIMB Accession No. 42335, which may comprise of the steps: a) preparing a progeny plant derived from hybrid spinach variety 51-521 RZ by crossing the plant of a spinach plant exhibiting a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15, representative seed of which have been deposited under NCIMB Accession No. 42335 with itself or a second spinach plant; b) crossing the progeny plant with itself or a second spinach plant to produce a seed of a progeny plant of a subsequent generation; c) growing a progeny plant of a subsequent generation from said seed and crossing the progeny plant of a subsequent generation with itself or a second spinach plant; and d) repeating step b) or c) for at least 1 more generation to produce an inbred spinach plant derived from the hybrid spinach variety 51-521 RZ.

The invention even further relates to a method of producing spinach which may comprise: (a) cultivating to the vegetative plant stage a plant of hybrid spinach variety 51-521 RZ, representative seed of which having been deposited under NCIMB Accession No. 42335, (b) harvesting spinach leaves from the plant, and (c) optionally using the harvested spinach leaves as a fresh vegetable or (d) optionally using the harvested spinach leaves as a processed food. The harvested spinach leaves of step (c) or step (d) may optionally have undergone one or more processing steps. Such a processing step might comprise but is not limited to any one of the following treatments or combinations thereof: cutting, washing, blanching, cooking, steaming, baking, pasteurizing, or freezing. The processed form that is obtained is also part of this invention. The invention further comprehends packaging the spinach leaves in fresh or processed form.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP § 2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, on Nov. 24, 2014, under deposit accession number NCIMB 42335 was made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawing, in which.

DETAILED DESCRIPTION OF THE INVENTION

The invention provides methods and compositions relating to plants, seeds and derivatives of a new hybrid spinach variety herein referred to as hybrid spinach variety 51-521 RZ. 51-521 RZ is a hybrid plant variety that is uniform and distinct from other such hybrids, and can be stably produced after a cycle of reproduction.

There are numerous steps in the development of any novel, plant with desirable characteristics. Selection of traits is a very important aspect of plant breeding. Once desirable traits are identified, the plants with those desirable traits are crossed in order to recombine the desirable traits and through selection, varieties or parent lines are developed. The goal is to combine in a single variety or hybrid an improved combination of desirable traits from the parent plant. These important traits may include but are not limited to higher yield, field performance, fruit and agronomic quality such as fruit shape, color and length, resistance to diseases and insects, and tolerance to drought and heat.

Choice of breeding or selection methods depends on the mode of plant reproduction, the heritability of the trait(s) being improved, and the type of cultivar used commercially (e.g., F1 hybrid cultivar, pureline cultivar, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach is used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

The development of commercial spinach hybrids relates to the development of spinach parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

Pedigree breeding is used commonly for the improvement of self-pollinating crops or inbred lines of cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new cultivars.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci may be routinely used and more alleles per marker locus may be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent. This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into spinach varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of double haploids may also be used for the development of homozygous lines in a breeding program. Double haploids are produced by the doubling of a set of chromosomes from a heterozygous plant to produce a completely homozygous individual. For example, see Wan et al., Theor. Appl. Genet., 77:889-892, 1989.

The spinach plant of the invention may be arrived at through crossing of inbred lines or through selection of the disclosed desirable characteristics by any of the breeding the selection methods mentioned above.

The parents of hybrid spinach variety 51-521 RZ were developed as follows: The mother is a spinach line made from pedigree selection from no. 08.49058. In total four selection, crossing and selfing cycles and one round of mass generation and selection was performed. The father line of 51-521 RZ is made from pedigree selection from no. GB.27207, obtained by three selection and inbreeding cycles, and two rounds of mass generation and selection. Crossing the described mother and father inbred spinach lines with one another will yield uniform F1 hybrid progeny plants. Table 1 shows the pedigree scheme of the mother line, Table 2 shows the pedigree scheme of the father line of hybrid spinach line 51-521 RZ.

TABLE 1

Breeding history of the mother line of 51-521 RZ.

| Year | | |
|---|---|---|
| Year 1 | F1 | pedigree selection from 08.49058 |
| Year 2 | S1 F1 | generation grown |
| Year 3 | S2 F1 | generation grown |
| Year 4 | S3 F1 | generation grown |
| Year 6 | M1 S3 F1 | generation grown (in mass) |

TABLE 2

Breeding history of the father line of 51-521 RZ.

| Year | | |
|---|---|---|
| Year 1 | F1 | pedigree selection from GB.27207 |
| Year 2 | S1 F1 | generation grown |
| Year 3 | S2 F1 | generation grown |
| Year 4 | S3 F1 | generation grown |
| Year 6 | M1 S3 F1 | generation grown (in mass) |
| Year 7 | M2 S3 F1 | generation grown (in mass) |

In one embodiment, a plant of the invention has all the morphological and physiological characteristics of spinach variety 51-521 RZ. These characteristics of a spinach plant of the invention, e.g. variety 51-521 RZ, are summarized and compared to its closest publicly available variety in Table 3.

The information presented in Table 3 was determined in trial experiments in accordance with the Exhibit C Form provided by the United States Department of Agriculture Plant Variety Protection Office. The terminology used in these tables is the official terminology found in the Exhibit C Form as of the filing date, and is thus clear for a person skilled in the art.

TABLE 3

Physiological and morphological characteristics of 51-521 RZ in comparison with closest known variety "Beaver RZ".

| Character | 51-521 RZ | Beaver RZ |
|---|---|---|
| Ploidy | Diploid | Diploid |
| Plant (Prime market stage): | | |
| Habit | Flat | Semi-erect |
| Size | Large | Large |
| Spread (cm) | 42 | 44 |
| Height (cm) | 13 | 17 |
| Seedling cotyledon | | |
| Width (mm) | 5 | 5 |
| Length (mm) | 45 | 53 |
| Tip | Round pointed | Round Pointed |
| Color chart | RHS 144A | RHS 137C |
| Leaf (First foliage leaves) | | |
| Shape | Cordate | Ovate |
| Base | Lobed | Lobed |
| Tip | Round pointed | Round pointed |
| Margin | Flat | Flat |
| Upper surface color chart | RHS 146A | RHS 137B |
| Lower surface color chart | RHS 146B | RHS 137C |
| Leaf (Prime market stage) | Leaf (Prime market stage) | Leaf (Prime market stage) |
| Surface | Smooth | Smooth |
| Shape | Ovate to Five Sided | Ovate to Five Sided |
| Base | Lobed | Lobed |
| Tip | Round-Pointed | Round |

TABLE 3-continued

Physiological and morphological characteristics of 51-521 RZ in comparison with closest known variety "Beaver RZ".

| Character | 51-521 RZ | Beaver RZ |
|---|---|---|
| Margin | Flat | Flat |
| Upper surface color chart | RHS 137B | RHS 137B |
| Lower surface color chart | RHS 137D | RHS 137D |
| Luster | Glossy | Glossy |
| Blade size | Medium | Small |
| Blade lobing | Not lobed | Not lobed |
| Petiole color | Light green | Light green |
| Color chart | RHS 137B | RHS 137B |
| Petiole red pigmentation | Absent | Absent |
| Petiole length to blade (cm) | 4.2 | 5.6 |
| Petiole diameter (mm) | 4 | 5 |

Aside from the morphological and physiological characteristics mentioned in Table 3, a plant of the invention also exhibits resistance to downy mildew (*Peronospora farinosa* f. sp. *spinaciae*).

As used herein, resistance to *Peronospora farinosa* f. sp. *spinaciae* is defined as the ability of a plant to resist infection by each of the various races Pfs1-Pfs15 in all stages between the seedling stage and the harvestable prime market stage.

The resistance to downy mildew infection was assayed as described by Irish et al. (2008; *Phytopathol.* 98: 894-900; incorporated herein by reference), using a differential set. Resistance is tested by inoculating plants at the true leaf stage, and observing symptoms of chlorosis and sporulation 7 days later.

As used herein resistance to *Peronospora farinosa* f. sp. *spinaciae* races Pfs1 to Pfs15, may be conferred by one or more resistance genes or a combination thereof, but most preferably partly by the single dominantly inherited R6 gene (See generally U.S. application Ser. No. 13/774,633 and U.S. application Ser. No. 13/872,011). The R6 gene is a single dominant gene conferring resistance against at least *Peronospora farinosa* f. sp. *spinaciae* races Pfs1, Pfs2, Pfs3, Pfs4, Pfs5, Pfs6, Pfs9, Pfs11, Pfs12, Pfs13 and Pfs14. In Table 4 the resistance pattern conferred by the R6 gene is compared with the resistance pattern as present in publicly available varieties. In Table 4 the *Peronospora farinosa* f. sp. *spinaciae* strains Pfs14 is included under its previous isolate name UA4410. Variety Lion is resistant to the same *Peronospora farinosa* f. sp. *spinaciae* races, however this resistance is conferred by multiple genes. This is demonstrated by including the parents of hybrid variety Lion. None of the parents is resistant to all of the *Peronospora farinosa* f. sp. *spinaciae* races Pfs1, Pfs2, Pfs3, Pfs4, Pfs5, Pfs6, Pfs9, Pfs11, Pfs12, Pfs13 and Pfs14, indicative that the genetic basis for the resistance pattern of Lion is multigenic, and caused by the stacking of at least two resistance genes. Therefore, it may be concluded that hybrid variety Lion does not comprise the single dominant R6 gene conferring resistance to *Peronospora farinosa* f. sp. *spinaciae* races Pfs1, Pfs2, Pfs3, Pfs4, Pfs5, Pfs6, Pfs9, Pfs11, Pfs12, Pfs13 and Pfs14.

Next to the deposit of hybrid spinach variety 51-521 RZ, a spinach plant which may comprise the R6 gene as present in hybrid variety 51-521 RZ has been deposited with NCIMB Ltd, Ferguson Building, Craibstone Estate, Bucksburn, Aberdeen AB21 9YA, UK, on Jul. 26, 2011, under deposit accession number NCIMB 41857.

TABLE 4

| Race | Viroflay | Resistoflay | Califlay | Clermont | Campania | Boeing | Lion | Lazio | Whale | Polka | Pigeon | R6 | Lion male parent | Lion female parent |
|---|---|---|---|---|---|---|---|---|---|---|---|---|---|---|
| Pfs: 1 | + | − | − | − | − | − | − | − | − | − | − | − | − | − |
| Pfs: 2 | + | − | + | − | − | − | − | − | − | − | − | − | − | + |
| Pfs: 3 | + | + | − | − | − | − | − | − | − | − | − | − | − | − |
| Pfs: 4 | + | + | + | − | − | − | − | − | − | + | − | − | − | + |
| Pfs: 5 | + | + | − | + | − | − | − | − | − | − | − | − | − | − |
| Pfs: 6 | + | + | + | + | + | − | − | − | − | + | − | − | − | + |
| Pfs: 9 | + | + | − | + | + | − | − | − | − | − | − | − | − | − |
| Pfs: 11 | + | + | − | + | − | − | − | + | − | − | − | − | − | − |
| Pfs12 | + | + | − | + | + | + | − | + | − | − | − | − | + | − |
| Pfs13 | + | + | (+) | + | (+) | − | − | + | + | (+) | − | − | − | (+) |
| UA4410 | + | + | − | + | + | + | − | + | − | − | + | − | + | − |

Figure 1:
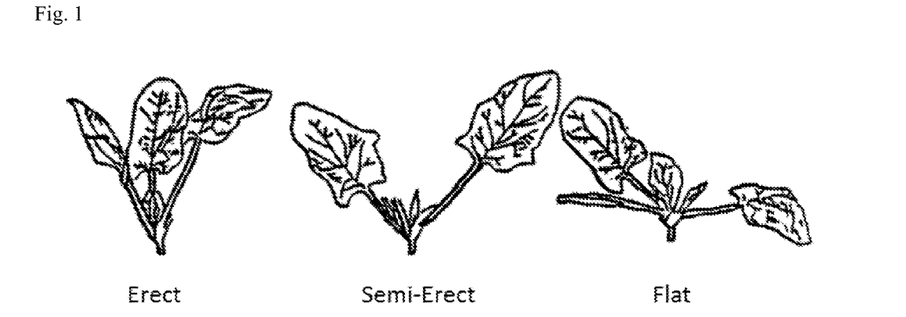
FIG. 1 is an illustration of the three different plant habits of plants at prime market stage grown under optimal conditions.
Figure 2:
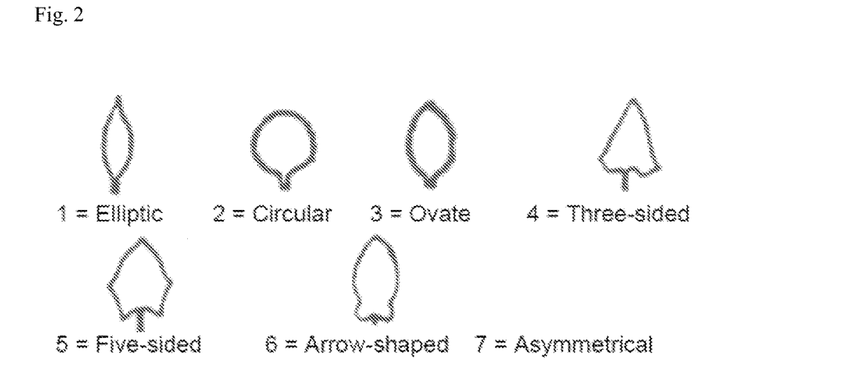
FIG. 2 is an illustration of seven different leaf shapes from plants at prime market stage grown under optimal conditions.

As used herein, plant habit is by visual comparison to standard varieties. Three different habits are recognized, and are shown in FIG. 1. "Flat", which is comparable to the habit of plants of variety Viroflay; "semi-erect", which is comparable to the habit of plants of variety Long Standing Bloomsdale; and "erect", which is comparable to the habit of plants of variety Virginia Savoy. Plants of hybrid variety 51-521 RZ have a flat plant habit, which is thus comparable to that of plants of variety Viroflay.

As used herein, the leaf surface is by visual comparison to standard varieties. Three different leaf surface types are recognised: smooth, semi-savoy, or savoy. Leaf surface is determined by comparison to standard varieties Viroflay, Northland, and Virginia Savoy. Viroflay has smooth leaves, Northland has semi-savoy leaves, while Virginia Savoy has savoy leaves. The leaf surface of hybrid spinach variety 51-521 RZ is smooth which is similar to the Viroflay variety.

Figure 3:
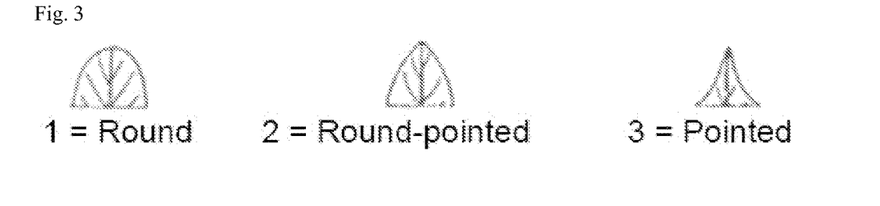
FIG. 3 is an illustration of three different leaf tip shapes from plants at prime market stage grown under optimal conditions.

As used herein, the leaf tip shape terminology is in concordance with that used on the Exhibit C Form provided by the United States Department of Agriculture Plant Variety Protection Office and are shown in FIG. 3. The mature leaves at prime market stage of hybrid spinach variety 51-521 RZ have a round pointed tip.

Hybrid spinach variety 51-521 RZ exhibits a field resistance to leaf spot disease anthracnose. Under normal growing conditions in the field plants that have a field resistance to anthracnose will normally show no or only very little symptoms of infection when the field gets infected with *Colletotrichum dematium* f. sp. *spinaciae*. In plants that have such a field resistance the disease symptoms, that include the formation of leaf spots, lesions and necrotic areas on leaves, develop later and at a slower rate than in susceptible plants. While the susceptible plants quickly perish due to these diseases, the plants that have a field resistance will remain relatively unaffected. The level of resistance of hybrid spinach variety 51-5221 RZ to *Colletotrichum dematium* f. sp. *spinaciae* is comparable to the resistance level to that disease found in publicly available spinach variety Novico and is stronger than the resistance level to that disease found in publicly available spinach variety Gazelle.

As used herein, growth rate is determined by comparison to publicly available varieties. Fast growing is defined as growing at a growth rate comparable to that of publicly available spinach varieties Sparrow and Beaver and growing at a growth rate that is lower than that of publicly available varieties Tapir and Rathlin. Hybrid spinach variety 51-521 RZ is a fast growing spinach variety which has a growth rate that is comparable to that of publicly available varieties Sparrow and Beaver and that is lower than that of publicly available varieties Tapir and Rathlin.

Hybrid spinach variety 51-521 RZ is a medium bolting variety. As used herein, bolting is defined in concordance with the definition on the UPOV TG/55/7 Form as the time it requires for 15% of the plants to begin to have a central flowering stem appear through the stretching of the internodes for spring sown crops. Bolting is determined by comparison to standard varieties Figo, Maracas, Bandola, Viroflay, Matador, Monnopa, Grappa, Medania, Revolver, Chica and Lavewa. Figo and Maracas are very early bolting varieties; Bandola and Viroflay are early bolting varieties; Matador and Monnopa are medium bolting varieties; Grappa, Medania and Revolver are late bolting varieties and Chica and Lavewa are very late bolting varieties. Hybrid spinach variety 51-521 RZ has a timing of bolting that is similar to that of Matador and Monnopa, and is therefore considered a medium bolting variety.

Embodiments of the invention advantageously have one or more, and most advantageously all, of these characteristics.

In an embodiment, the invention relates to spinach plants that have all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that may be introduced into a hybrid by backcrossing the trait into one or both parents, useful traits may be introduced directly into the plant of the invention, being a plant of hybrid spinach variety 51-521 RZ, by genetic transformation techniques; and, such plants of hybrid spinach variety 51-521 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of hybrid spinach variety 51-521 RZ or may, alternatively, be used for the preparation of transgenes which may be introduced by backcrossing. Methods for the transformation of plants, including spinach, are well known to those of skill in the art.

Vectors used for the transformation of spinach cells are not limited so long as the vector may express an inserted DNA in the cells. For example, vectors which may comprise promoters for constitutive gene expression in spinach cells (e.g., cauliflower mosaic virus 35S promoter) and promoters inducible by exogenous stimuli may be used. Examples of suitable vectors include pBI binary vector. The "spinach cell" into which the vector is to be introduced includes various forms of spinach cells, such as cultured cell suspensions, protoplasts, leaf sections, and callus. A vector may be introduced into spinach cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target spinach cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of spinach variety 51-521 RZ.

*Agrobacterium*-mediated transfer is another widely applicable system for introducing gene loci into plant cells. An advantage of the technique is that DNA may be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes may be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including spinach plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for spinach plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from spinach (psaD, psaF, psaE, PC, FNR, atpC, atpD, cab, rbcS) (see U.S. Pat. No. 7,161,061), the CAB-1 promoter from spinach (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the spinach variety of this invention include, for example, DNA sequences or genes from another species, or even genes or sequences which originate with or are present in spinach species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of spinach variety 51-521 RZ. Non-limiting examples of particular genes and corresponding phenotypes one may choose to introduce into a spinach plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that may concern transformed spinach and/or methods of transforming spinach or spinach plant cells, and techniques from these US Patents, as well as promoters, vectors, etc., may be employed in the practice of this invention to introduce exogenous nucleic acid sequence(s) into a plant of spinach variety 51-521 RZ (or cells thereof), and exemplify some exogenous nucleic acid sequence(s) which may be introduced into a plant of spinach variety 51-521 RZ (or cells thereof) of the invention, as well as techniques, promoters, vectors etc., to thereby obtain further plants of spinach variety 51-521 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems (See generally U.S. Pat. No. 7,041,876 on spinach being recognized as a plant that may be regenerated from cultured cells or tissue).

Also, the invention comprehends methods for producing a seed of a "51-521 RZ"-derived spinach plant which may comprise (a) crossing a plant of spinach variety 51-521 RZ, representative seed of which having been deposited under NCIMB Accession No. 42335, with a second spinach plant, and (b) whereby seed of a "51-521 RZ"-derived spinach plant forms. Such a method may further comprise (c) crossing a plant grown from "51-521 RZ"-derived spinach seed with itself or with a second spinach plant to yield additional "51-521 RZ"-derived spinach seed, (d) growing the additional "51-521 RZ"-derived spinach seed of step (c) to yield additional "51-521 RZ"-derived spinach plants, and (e) repeating the crossing and growing of steps (c) and (d) for an additional 3-10 generations to further generate "51-521 RZ"-derived spinach plants.

The invention further relates to the above methods that may further comprise selecting at steps b), d), and e), a "51-521 RZ"-derived spinach plant exhibiting a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

In particular, the invention relates to methods for producing a seed of a "51-521 RZ"-derived spinach plant which may comprise (a) crossing a plant of spinach variety 51-521 RZ, representative seed of which having been deposited under NCIMB Accession No. 42335, with a second spinach plant and (b) whereby seed of a 51-521 RZ-derived spinach plant forms, wherein such a method may further comprise (c) crossing a plant grown from 51-521 RZ-derived spinach seed with itself or with a second spinach plant to yield additional 51-521 RZ-derived spinach seed, (d) growing the additional 51-521 RZ-derived spinach seed of step (c) to yield additional 51-521 RZ-derived spinach plants and selecting plants exhibiting a combination of the traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15, and (e) repeating the crossing and growing of steps (c) and (d) for an additional 3-10 generations to further generate 51-521 RZ-derived spinach plants that exhibit a combination of traits fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

Backcrossing one of the parents of a hybrid may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The invention additionally provides a method of introducing a desired trait into a plant of hybrid spinach variety 51-521 RZ by reverse breeding (See generally U.S. application Ser. No. 10/487,468, published as 2006-0179498 A1), which may comprise the following steps: (a) allowing the hybrid spinach plant to produce haploid cells, while suppressing recombination, (b) growing haploid plants into diploid plants, (c) selecting those homozygous plants which together constitute the hybrid variety of the invention as parent plants for the said hybrid, (d) crossing one of the said parent plants with a plant which may have the desired trait, (e) crossing the selected F1 progeny with said parent plant, to produce backcross progeny; (f) selecting backcross progeny which may comprise the desired trait and the physiological and morphological characteristic of the parent plant; and, optionally, (g) repeating steps (e) and (f) one or more times in succession to produce selected fourth or higher backcross progeny that may comprise the desired trait and all of the physiological and morphological characteristics of said parent plant, (h) crossing the backcrossed parent plant having the added desired trait with the other parent plant obtained after reverse breeding to obtain a plant which may comprise the desired trait and all of the physiological and morphological characteristics of a plant of spinach variety 51-521 RZ.

The invention further involves a method of determining the genotype of a plant of spinach variety 51-521 RZ, representative seed of which has been deposited under NCIMB Accession No. 42335, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of spinach variety 51-521 RZ.

There are various ways of obtaining genotype data from a nucleic acid sample. Genotype data may be gathered which is specific for certain phenotypic traits (e.g. gene sequences), but also patterns of random genetic variation may be obtained to construct a so-called DNA fingerprint. Depending on the technique used a fingerprint may be obtained that is unique for hybrid spinach variety 51-521 RZ. Obtaining a unique DNA fingerprint depends on the genetic variation present in a variety and the sensitivity of the fingerprinting technique. A technique known in the art to provide a good fingerprint profile is called the AFLP fingerprinting technique (See generally U.S. Pat. No. 5,874,215), but there are many other marker-based techniques, such as RFLP (or Restriction fragment length polymorphism), SSLP (or Simple sequence length polymorphism), RAPD (or Random amplification of polymorphic DNA), VNTR (or Variable number tandem repeat), Microsatellite polymorphism, SSR (or Simple sequence repeat), STR (or Short tandem repeat), SFP (or Single feature polymorphism), DArT (or Diversity Arrays Technology), RAD markers (or Restriction site associated DNA markers) (e.g. Semagn et al. African Journal of Biotechnology Vol. 5 number 25 pp. 2540-2568, 29 Dec. 2006; Baird et al. PloS ONE Vol. 3 number 10 e3376, 2008). Nowadays, sequence-based methods are utilising Single Nucleotide Polymorphisms (SNPs) that are randomly distributed across genomes, as a common tool for genotyping (eg. Elshire et al. PloS ONE Vol. 6 number 5 e19379, 2011; Poland et al. PloS ONE Vol. 7 number 2 e32253, 2012; Truong et al. PloS ONE Vol. 7 number 5 e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species. It is possible, for example, to detect polymorphisms for the characteristic of the resistance to downy mildew (*Peronospora farinosa* f. sp. *spinaciae*) races Pfs1 to Pfs15 by comparing the genotype and/or the sequence of spinach variety 51-521 RZ with the genotype and/or the sequence of one or more reference plants. The reference plant(s) used for comparison may for example be, but is not limited to, the comparison variety Tapir. It is also possible, for example, to detect polymorphisms for the characteristic of the field resistance to *Colletotrichum dematium* f. sp. *spinaciae* by comparing the genotype and/or the sequence of spinach variety 51-521 RZ with the genotype and/or the sequence of one or more reference plants. The reference plant(s) used for comparison may for example be, but is not limited to, the comparison variety Tapir or Gazelle.

The polymorphisms revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

Spinach leaves are sold in packaged form, including without limitation as pre-packaged spinach salad or as canned spinach or as frozen spinach. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach of the invention, as well as leaves of spinach derived from the invention.

The invention further relates to a container which may comprise one or more plants of the invention, or one or more spinach plants derived from a plant of the invention, in a growth substrate for harvest of leaves from the plant in a domestic environment. This way the consumer may pick very fresh leaves for use in salads. More generally, the invention includes one or more plants of the invention or one or more plants derived from spinach of the invention, wherein the plant is in a ready-to-harvest condition, including with the consumer picking his own, and further including a container which may comprise one or more of these plants.

The invention is further described by the following numbered paragraphs:

1. A spinach plant designated 51-521 RZ, representative seed of which having been deposited under NCIMB Accession No. 42335, wherein said plant comprises at least the following combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

2. The spinach plant of paragraph 1 wherein the plant has round pointed mature leaves.

3. A seed of the plant of paragraph 1.

4. A part of the plant of paragraph 1, wherein said part of the plant is suitable for sexual reproduction.

5. A part of the plant as described in paragraph 4, wherein said part is selected from the group consisting of a microspore, pollen, an ovary, an ovule, an embryo sac and an egg cell.

6. A part of the plant of paragraph 1, wherein said part of the plant is suitable for vegetative reproduction.

7. A part of the plant as described in paragraph 6, wherein said part is selected from the group consisting of a cutting, a root, a stem, a cell and a protoplast.

8. A tissue culture of regenerable cells from the spinach plant of paragraph 1.

9. The tissue culture as described in paragraph 8, wherein said cell or protoplast of the tissue culture is derived from a tissue selected from the group consisting of a leaf, pollen, an embryo, a cotyledon, a hypocotyl, a meristematic cell, a root, a root tip, an anther, a flower, a seed and a stem.

10. A spinach plant exhibiting a combination of traits comprising fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15, and having genetic material for so exhibiting the combination of traits; wherein the genetic information is as contained in a plant, representative seed of which having been deposited under NCIMB Accession No. 42335.

11. Progeny of the plant of paragraph 10, wherein said progeny is produced by sexual or vegetative reproduction of said spinach plant, and wherein said progeny exhibits a combination of traits comprising fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15 and has genetic material for so exhibiting the combination of traits; wherein the genetic information is as contained in a plant, representative seed of which having been deposited under NCIMB Accession No. 42335.

12. A method for producing a progeny plant of the spinach plant of paragraph 1, comprising crossing the plant of paragraph 1 with itself or with another spinach plant, harvesting the resultant seed, and growing said seed into a progeny plant.

13. A progeny plant produced by the method of paragraph 12, wherein said progeny plant exhibits a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

14. The progeny plant as defined in paragraph 11 or paragraph 13, wherein said progeny plant is modified in one or more characteristics.

15. The progeny plant as defined in paragraph 14, wherein the modification is effected by mutagenesis.

16. The progeny plant as defined in paragraph 14, wherein the modification is effected by transformation with a transgene.

17. A method for producing spinach leaves comprising: a) obtaining a plant according to paragraph 1, wherein the plant has been cultivated to obtain leaves; and b) harvesting the spinach leaves from the plant.

18. A method for producing spinach leaves as a fresh vegetable comprising packaging the leaves of the plant of paragraph 1.

19. A method for producing spinach leaves as a processed food comprising processing the leaves of the plant of paragraph 1.

20. One or more spinach plants of paragraph 1, in a container, for the harvest of leaves.

21. A spinach plant having all morphological and physiological characteristics of a spinach plant, representative seed of which having been deposited under NCIMB Accession No. 42335.

22. A method for producing a seed of a hybrid spinach variety 51-521 RZ-derived spinach plant comprising the steps of: (a) crossing a spinach plant of hybrid spinach variety 51-521 RZ, representative seed of which having been deposited under NCIMB Accession Number 42335, with a second spinach plant or with itself; and (b) allowing seed of a 51-521 RZ-derived spinach plant to form.

23. The method of paragraph 22, further comprising the steps of: (c) selfing a plant grown from said 51-521 RZ-derived spinach seed or crossing it to a second spinach plant to yield additional 51-521 RZ-derived spinach seed; (d) growing said additional 51-521 RZ-derived spinach seed of step (c) to yield additional 51-521 RZ-derived spinach plants; and (e) repeating the crossing and growing steps of (c) and (d) for an additional 3-10 generations to generate further 51-521-derived spinach plants, and (f) allowing seed of a 51-521-derived spinach plant to form.

24. The method of paragraph 25 further comprising selecting at steps b), d) and e), a 51-521 RZ-derived spinach plant, exhibiting a combination of traits including fast growing, a flat plant habit, smooth mature leaves, a field resistance against *Colletotrichum dematium* f. sp. *spinaciae* and resistance to downy mildew (*P. farinosa* f. sp. *spinaciae*) races Pfs1 to Pfs15.

25. A spinach seed produced by the method of any of the paragraphs 22, 23 or 24.

26. A spinach plant grown from the seed of paragraph 25.

27. A method of determining the genotype of a plant of hybrid spinach variety 51-521 RZ, representative seed of which has been deposited under NCIMB Accession No. 42335, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of hybrid spinach variety 51-521 RZ and/or give rise to the expression of any one or more, or all, of the morphological and physiological characteristics of hybrid spinach variety 51-521 RZ of paragraph 32.

28. The method of paragraph 27 additionally comprising the step of storing the results of detecting the plurality of polymorphisms on a computer readable medium, or transmitting the results of detecting the plurality of polymorphisms.

29. The spinach plant of paragraph 1, which is a plant grown from seed having been deposited under NCIMB accession No. 42335.

30. A seed of hybrid spinach variety 51-521 RZ, a sample of seed of said hybrid variety having been deposited under NCIMB Accession Number 42335.

31. A plant grown from the seed of paragraph 30.

32. The spinach plant of paragraph 31, which is a plant grown from seed having been deposited under NCIMB Accession Number 42335.

33. A spinach plant, or a part thereof, having all the physiological and morphological characteristics of the spinach plant of paragraph 31.

34. A part of the plant of paragraph 31, wherein said part is a microspore, pollen, an ovary, an ovule, an embryo sac, an egg cell, a cutting, a root, a stem, a cell or a protoplast.

35. A tissue culture of regenerable cells or protoplasts from the plant part of paragraph 34.

36. The tissue culture of paragraph 35, wherein said cells or protoplasts of the tissue culture are derived from a leaf, pollen, an embryo, a cotyledon, a hypocotyl, a meristematic cell, a root, a root tip, an anther, a flower, a seed or a stem.

37. A spinach plant regenerated from the tissue culture of paragraph 35 or 36, wherein the regenerated plant expresses all of the physiological and morphological characteristics of hybrid spinach variety 51-521 RZ, a sample of seed of said hybrid having been deposited under NCIMB Accession Number 42335.

38. A method of vegetatively propagating a plant of hybrid spinach variety 51-521 RZ comprising the steps of: (a) collecting tissue capable of being propagated from a plant of hybrid spinach variety 51-521 RZ, representative seed of said hybrid spinach variety having been deposited under NCIMB Accession Number 42335; and (b) producing a rooted plant from said tissue.

39. A method of producing a spinach seed, comprising crossing the plant of claim 32 with itself or a second spinach plant.

40. A spinach seed produced by the method of paragraph 39.

41. A spinach plant grown from the seed as claimed in claim 40.

42. A method of producing a plant of spinach hybrid variety 51-521 RZ comprising at least one new trait, the method comprising introducing a mutation or transgene conferring the at least one new trait into a plant of hybrid spinach variety 51-521 RZ, wherein a sample of seed of said variety has been deposited under NCIMB Accession Number 42335.

43. The spinach plant produced by the method of claim 42.

44. A method of producing spinach leaves comprising: (a) obtaining a plant according to paragraph 31, wherein the plant has been cultivated to obtain leaves; and (b) harvesting spinach leaves from the plant to thereby obtain harvested spinach leaves.

45. The method of paragraph 44 further comprising packaging the harvested spinach leaves as a fresh vegetable.

46. The method of paragraph 44 further comprising processing the harvested spinach leaves as a processed food.

47. A container comprising one or more spinach plants of paragraph 31 for harvest of leaves.

48. A plant of spinach hybrid variety 51-521 RZ comprising a transgene conferring a desired trait, a sample of seed of said variety has been deposited under NCIMB Accession Number 42335.

49. A seed that produces the plant of paragraph 48.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A seed of hybrid spinach variety 51-521 RZ, a sample of seed of said hybrid variety having been deposited under NCIMB Accession Number 42335.

2. A plant grown from the seed of claim 1.

3. The spinach plant of claim 2, which is a plant grown from seed having been deposited under NCIMB Accession Number 42335.

4. A spinach plant, or a part thereof, having all the physiological and morphological characteristics of the spinach plant of claim 2.

5. A part of the plant of claim 2, wherein said part is a microspore, pollen, an ovary, an ovule, an embryo sac, an egg cell, a cutting, a root, a stem, a cell or a protoplast.

6. A tissue culture of regenerable cells or protoplasts from the plant part of claim 5.

7. The tissue culture as claimed in claim 6, wherein said cells or protoplasts of the tissue culture are derived from a leaf, pollen, an embryo, a cotyledon, a hypocotyl, a meristematic cell, a root, a root tip, an anther, a flower, a seed or a stem.

8. A spinach plant regenerated from the tissue culture of claim 6, wherein the regenerated plant expresses all of the physiological and morphological characteristics of hybrid spinach variety 51-521 RZ, a sample of seed of said hybrid having been deposited under NCIMB Accession Number 42335.

9. A method of vegetatively propagating a plant of hybrid spinach variety 51-521 RZ comprising the steps of:
 (a) collecting tissue capable of being propagated from a plant of hybrid spinach variety 51-521 RZ, representative seed of said hybrid spinach variety having been deposited under NCIMB Accession Number 42335; and
 (b) producing a rooted plant from said tissue.

10. A method of producing a spinach seed, comprising crossing the plant of claim 2 with itself or a second spinach plant.

11. A method for producing a seed of a hybrid spinach variety 51-521 RZ-derived spinach plant comprising the steps of:
(a) crossing a spinach plant of hybrid spinach variety 51-521 RZ, representative seed of which having been deposited under NCIMB Accession Number 42335, with a second spinach plant or with itself; and
(b) allowing seed of a 51-521-derived spinach plant to form.

12. The method of claim 11, further comprising the steps of:
(c) selfing the plant grown from said 51-521 RZ-derived spinach seed or crossing it to a second spinach plant to yield additional 51-521 RZ-derived spinach seed;
(d) growing said additional 51-521 RZ-derived spinach seed of step (c) to yield additional 51-521 RZ-derived spinach plants; and
(e) repeating the crossing and growing steps of (c) and (d) for an additional 3-10 generations to generate further 51-521 RZ-derived spinach plants, and
(f) allowing seed of the further 51-521 RZ-derived spinach plant to form.

13. A method of producing a plant of spinach hybrid variety 51-521 RZ comprising at least one new trait, the method comprising introducing a mutation or transgene conferring the at least one new trait directly into a plant of hybrid spinach variety 51-521 RZ, wherein a sample of seed of said variety has been deposited under NCIMB Accession Number 42335.

14. The spinach plant produced by the method of claim 13.

15. A method of producing spinach leaves comprising:
(a) obtaining a plant according to claim 2, wherein the plant has been cultivated to obtain leaves; and
(b) harvesting spinach leaves from the plant to thereby obtain harvested spinach leaves.

16. The method of claim 15 further comprising packaging the harvested spinach leaves as a fresh vegetable.

17. The method of claim 15 further comprising processing the harvested spinach leaves as a processed food.

18. A container comprising one or more spinach plants of claim 2 for harvest of leaves.

19. A method of determining the genotype of a plant of hybrid spinach variety 51-521 RZ, representative seed of which has been deposited under NCIMB Accession No. 42335, or a first generation progeny thereof, comprising
obtaining a sample of nucleic acids from said plant and
comparing said nucleic acids to a sample of nucleic acids obtained from a reference plant, and detecting a plurality of polymorphisms between the two nucleic acid samples,
wherein the plurality of polymorphisms are indicative of hybrid spinach variety 51-521 RZ and/or give rise to the expression of any one or more, or all, of the morphological and physiological characteristics of hybrid spinach variety 51-521 RZ as claimed in claim 2.

20. A plant of spinach hybrid variety 51-521 RZ comprising a transgene conferring a desired trait, a sample of seed of said variety has been deposited under NCIMB Accession Number 42335.

21. A seed that produces the plant of claim 20.

* * * * *